United States Patent [19]

Cooper et al.

[11] Patent Number: 4,646,765

[45] Date of Patent: Mar. 3, 1987

[54] NAIL COMPOSITIONS CONTAINING CYANOACRYLATE AND GRAPHITE

[76] Inventors: Donald E. Cooper; David A. Cooper, both of 5319 SW. Westgate Dr., Suite 113, Portland, Oreg. 97221

[21] Appl. No.: 825,220

[22] Filed: Feb. 3, 1986

[51] Int. Cl.$^4$ ............... A45D 29/00; A45D 31/00; C08K 3/04

[52] U.S. Cl. ............... 132/73; 252/511; 424/61; 427/155; 523/105; 524/496; 524/700; 524/850

[58] Field of Search ............... 524/496, 700, 850; 523/105; 132/73; 424/61; 427/155; 252/511

[56] References Cited

U.S. PATENT DOCUMENTS

| | | | |
|---|---|---|---|
| 2,794,788 | 6/1957 | Coover et al. | 524/850 |
| 3,301,760 | 1/1967 | Jewel | 167/85 |
| 3,342,686 | 1/1967 | Jewel et al. | 167/85 |
| 3,478,756 | 11/1969 | Sautter et al. | 132/73 |
| 3,896,077 | 7/1975 | Leonard et al. | 524/850 |
| 4,007,748 | 2/1977 | Matranga et al. | 132/73 |
| 4,104,333 | 8/1978 | Lee, Jr. et al. | 260/885 |
| 4,229,431 | 10/1980 | Lee, Jr. et al. | 424/61 |
| 4,260,701 | 4/1981 | Lee, Jr. | 525/303 |
| 4,405,750 | 9/1983 | Nakata et al. | 524/850 |
| 4,407,310 | 10/1983 | Jadow | 132/73 |
| 4,440,910 | 4/1984 | O'Connor | 525/295 |
| 4,465,092 | 8/1984 | Vitale | 137/385 |
| 4,495,172 | 1/1985 | Orlowski et al. | 424/61 |
| 4,526,636 | 7/1985 | Mader | 427/203 |
| 4,547,363 | 10/1985 | Joos | 424/61 |

FOREIGN PATENT DOCUMENTS

| | | | |
|---|---|---|---|
| 2902029 | 8/1979 | Fed. Rep. of Germany | 132/73 |
| 2451724 | 11/1980 | France | 132/73 |
| 0226077 | 12/1984 | Japan | 132/73 |
| 0118776 | 6/1985 | Japan | 252/511 |

OTHER PUBLICATIONS

Chem. Abs. 87-153082z (1977).

*Primary Examiner*—Herbert J. Lilling
*Attorney, Agent, or Firm*—Klarquist, Sparkman, Campbell, Leigh & Whinston

[57] ABSTRACT

A composition for adhering to human nails includes a mixture of a cyanoacrylate compound and/or graphite fibers. Such composition can take the form of either an artificial nail extender or a nail coating. The composition for forming an artificial nail includes graphite fibers, a cyanoacrylate, and a hardening accelerator containing a mixture of trichlorotrifluoroethane and N,N-dimethyl-P-toluidine. The accelerator is adapted to be sprayed onto a base material containing the graphite fibers and cyanoacrylate in the form of a mist. Nail compositions containing graphite fibers have significantly increased strength yet remain flexible to allow for flexure of the nail. The cyanoacrylate compounds increase the chemical bonding of the compositions to a nail.

23 Claims, No Drawings

NAIL COMPOSITIONS CONTAINING CYANOACRYLATE AND GRAPHITE

BACKGROUND OF THE INVENTION

This invention relates generally to nail compositions. More particularly, the invention relates to nail compositions for coating nails and for extending nails.

Nail compositions can take varying forms, for example, nail coatings in the form of nail polishes and removers. Other compositions are designed for forming artificial nail extensions for lengthening or mending nails. Such compositions must be easy to apply and non-yellowing to be acceptable to a consumer.

Present state-of-the-art nail extender and repair compositions are generally described in U.S. Pat. Nos. 3,478,756 to Sautter et al., 4,104,333 to Lee, Jr. et al, 4,229,431 to Lee, Jr. et al, and 4,260,701 to Lee, Jr. Such compositions are available in the form of kits containing acrylic polymers in one container and a separate container of activator compounds. The polymers and activator when mixed form a doughy material which is troweled onto the upper surface of the existing nail and onto a template positioned at the end of the nail to form the extension. Drying time upon forming is several minutes before the forming template can be safely removed. Such products have the drawback of being slow to mix from two containers onto a mixing surface and having a short shelf or pot life. The mixture produced is also thick and hard to form. In addition, the texture of the hardened nail is generally quite rough requiring many minutes of filing to smooth the surface into an acceptable shape and finish. Furthermore, the resulting nail extension is commonly so hard that it is brittle and easily breaks, or so flexible that it lacks strength.

Current state-of-the-art nail coatings such as nail polishes have similar drawbacks. Such nail polishes are commonly comprised of nitrocellulose and polymer resins which do not bond properly to the nail keratin. Accordingly, a user must repolish the nails often as the polish chips away. Nail polishes also do not provide much added strength to an existing nail. Hardening nail coatings are known but also lack proper adhesion and become so brittle that they crack and break upon impact with hard objects. Such products have increased strength over ordinary nail polishes, but lack flexibility and bonding power. Nail coatings having drawbacks such as these are described in U.S. Pat. Nos. 4,495,172 to Orlowski et al., 4,547,363 to Joos, 3,301,760 to Jewel, 3,342,686 to Jewel et al., and 4,407,310 to Jadow.

SUMMARY OF THE INVENTION

It is an object of the present invention to provide a nail composition which upon hardening forms a coating which is strong and flexible.

Another object of the present invention is to provide an artificial nail extender or repair composition that can be applied to a nail by both professional applicators and average consumers.

Still another object of the present invention is to provide a nail extender or repair composition which is inert to body tissue.

Yet another object of the present invention is to provide a nail extender or repair composition which rapidly hardens upon application of an accelerator.

Another object of the present invention is to provide a nail coating having greater adhesion to a nail.

Yet still another object of the present invention is to provide a nail coating which is non-irritating to the cuticle and inert to body tissue.

Still a further object of the present invention is to provide a nail coating which is inert to detergent solutions.

Yet another object of the present invention is to provide a nail coating which is color compatible with various tints.

Still a further object of the present invention is to provide a nail coating which when applied and dried has great film strength to resist abrasion and chipping.

Yet another object of the present invention is to provide such a nail coating which is thin, flexible, yet strong.

The foregoing objects are achieved by the nail compositions of the present invention. Such compositions include graphite fibers and/or cyanoacrylate compounds.

These and other objects, advantages, and features of the invention will become more readily apparent from the following detailed description.

DETAILED DESCRIPTION

There are two aspects of the present invention. First, cyanoacrylate compounds in nail coatings have been discovered to greatly increase the adherence of a coating to a nail. Second, graphite fibers have been discovered to be useful in nail composition to significantly increase the strength of the hardened composition applied to nails. The nail compositions of the present invention can be in the form of artificial nail extender and repair compositions, or nail coatings.

Artificial Nail Extender and Repair Compositions

The base material for the artificial nail composition of this embodiment of the invention comprises a mixture of a cyanoacrylate compound and graphite fibers which forms a base material. This base material hardens when mixed with a hardening accelerator which includes a mixture of trichloro-trifluoroethane and a methylaniline compound, such as N,N-dimethyl-P,toluidine. The hardened product when coated on a nail and an attached template forms a nail extension that is strong and flexible.

The graphite fibers in the base material are translucent graphite fibers which are whitish in color and provide an artificial nail which is translucent and thereby natural appearing. Such graphite fibers can be purchased from Hercules Incorporated, 910 Market St., Wilmington, Del. 19899, as the precursor, or raw, graphite fiber. It is the raw, precursor form of the graphite fiber which is preferred as it is this fiber that has the whitish color. Precursor graphite fibers can also be purchased from the Courtalds Company of Coventry, England. The graphite fibers usable for the instant invention can be round and vary in diameter from 0.3 mils to 0.75 mils. Most preferred are round fibers having a diameter ranging from 0.3 mils to 0.4 mils. The fibers can be present in the base material in a concentration ranging from 1.0% to 4.0% by weight. Most preferred is a concentration ranging from 2.0% to 4.0% by weight of the base material.

The fibers can be of uniform length but are preferably of varying lengths, from 1/32 inch to 6/32 inch. Most preferred are fibers varying in length from 1/32 inch to 5/32 inch. It is also preferred that the medium length, for example the 2/32 inch and 3/32 inch, fibers predominate over the long, 5/32 inch, and short, 1/32 inch, fibers. This variety of length provides a smoother finished matrix of maximum strength and flexure.

Any of a variety of cyanoacrylate compounds or mixtures of cyanoacrylate compounds can be used. The viscosity of the cyanoacrylate compound or compounds used for the extender repair compositions should be from 500 centipoise to 2,500 centipoise in viscosity. Most preferred are cyanoacrylate compositions having a viscosity somewhere between 800 centipoise and 2,000 centipoise.

The accelerator is adapted to be applied to the base material by spraying it thereon in the form of a mist, as more fully described below. The accelerator includes a mixture of trichloro-trifluoroethane and a methylaniline such as N,N-dimethyl-P-toluidine. The trichloro-trifluoroethane can be present in the accelerator in a concentration ranging from 35% to 60% by weight. Most preferred is a concentration ranging from 40% to 50% by weight. The N,N-dimethyl-P-toluidine can be present in the accelerator in a concentration ranging from 20% to 40% by weight. Most preferred is a concentration ranging from 25% to 30% by weight. Preferably the accelerator is augmented with ethyl chloride which further accelerates the curing time of the matrix and enhances the dispersion of any heat generated. The ethyl chloride can be present in the accelerator in a concentration ranging from 15% to 40% by weight of the accelerator. Most preferred is a concentration ranging from 20% to 30% by weight of the accelerator. Liquid freon is also usable as an accelerator and cooling agent.

Acrylic polymers can also be added to the accelerator to enhance the smoothness of the resulting matrix. The acrylic polymers can be present in a concentration ranging from 1.0% to 5.0% by weight of the accelerator. Most preferred is a concentration ranging from 2.0% to 4.0% by weight of the accelerator.

When acrylic polymers are used, it is desirable to add an aromatic scent to the accelerator to counteract the polymer odor. Such aromatic scents can be included in the accelerator in concentrations ranging from 0.01% to 1.0% by weight of the accelerator.

It is recommended, although not necessary, that the nail and cuticle be sterilized as by swabbing the same with hydrogen peroxide or another conventional sterilizing solution prior to applying the extender and repair composition. This will reduce the possibility of any trapped bacteria starting an infection after the composition has been applied. The base material can be brushed or applied by spatula to a template positioned at the end of the nail to be extended or reconstructed. A thin coat of base material should extend back to the half-moon of the nail to provide a sufficiently large surface area for adhering the extension to the nail to prevent the extension from separating from the nail after hardening.

After the base material is applied to the template and existing nail and formed to the desired shape, the accelerator is sprayed onto the base material in the form of a mist. This causes the mixture to harden almost instantly into a flexible, durable artificial nail which can be filed or polished similar to a natural nail. The accelerator mist cures the cyanoacrylategraphite fiber matrix within three seconds without irritation to the surrounding skin or cuticle. The heat generated by the polymerization of the matrix is dissipated by the vaporization of the mist. Various tinting materials can be incorporated into the base material if so desired to impart a color throughout the artificial nail. Nail polishes can be applied to the hardened artificial nail as with natural nails.

The nail extender composition is also usable to repair chipped or otherwise damaged nails without causing the nail to be extended by troweling the base material to the damaged area followed by application of the accelerator to cause it to harden.

EXAMPLE I

A base material was prepared having the following composition by weight:

| | |
|---|---|
| Cyanoacrylate (2000+/−400 centipoise) | 96.4% |
| Graphite fiber | 3.6% |
| | 100.0% |

The graphite fibers had a diameter of 0.31 mils and were present in lengths varying from 1/32 inch to 5/32 inch in the following proportions:

| | |
|---|---|
| 1/32 inch | 10% |
| 2/32 inch | 40% |
| 3/32 inch | 40% |
| 5/32 inch | 10% |
| | 100% |

A liquid accelerator material was prepared having the following compositions by weight:

| | |
|---|---|
| trichloro-trifluoroethane | 47.4% |
| N,N—dimethyl-P—toluidine | 26.3% |
| ethylene glycol dimethlacrylate | 2.0% |
| aromatic scent | 0.6% |
| ethyl chloride | 23.7% |
| | 100.0% |

The nail to be extended was disinfected with a cotton ball moistened in a disinfectant solvent sold under the trademark Cuti-Clean ™. Thereafter, the nail surface was lightly sanded to remove any oily glaze from the nail to facilitate adhesion of the base material to the nail. A template made of teflon for forming the nail extension was positioned at the end of and just underneath the nail to be extended. Teflon is used as a material for the template as it does not stick to the base material before or after hardening. The base material in the form of a cream was applied to the nail and template with a spatula. The base material was applied first to the back end of the nail near the half-moon and troweled forward onto the teflon template for forming the shape of the desired nail. The base material remains workable until the accelerator is applied for achieving the desired shape.

The accelerator was sprayed onto the base material in the form of a mist with a suitable mist applicator in one thorough spray covering the upper surface of the base material which hardened the base material in about one second. The teflon template was then carefully removed from the underside of the formed extension. Thereafter the extended nail was filed to the desired final shape and finish.

Nail Coating Compositions

Cyanoacrylates have been discovered as useful in nail coating compositions to significantly improve the adhesion of the coating to the nail. The cyanoacrylate compounds bond chemically to the fingernail keratin thus minimizing chipping. When combined with the graphite fibers used in the artificial nail composition described above, a strong, flexible nail coating results which readily adheres to the surface of a nail.

As with the extender/repair composition, any of a variety of cyanoacrylate compounds or mixtures of cyanoacrylate compounds can be used. It is preferable that the viscosity of the cyanoacrylate portion be thinner than that of the extender/repair composition. For example, for nail coatings the viscosity range should be from 100 centipoise to 600 centipoise, with 150 centipoise to 300 centipoise being the preferred range.

Two methods may be used for applying coatings to nails. One such method is a two step process wherein a base coat is applied to a nail followed by a top coat after the base coat has dried. Another such method is a one step process which entails the application of just a single coat to the nail. The nail coating compositions of the instant invention include a base coat product and top coat product, usable in the two step process, and a single coat product usable in the one step process. The base coat, top coat, and single coat products should each include at least fifty percent nitrocellulose as a carrier material.

The base coat product should be a relatively thick material, heavy in both fiber and cyanoacrylate to provide strong bonding and high flexure strength. For example, it should contain from 0.01% to 0.030% graphite fibers and from 1.0% to 4.0% cyanoacrylate. The preferred range is from 0.020% to 0.030% graphite fibers and from 2.0% to 3.0% cyanoacrylate.

The top coat product is a relatively thin material and light in both fiber and cyanoacrylate, since those properties are provided by the base coat. It should contain from 0.003% to 0.010% graphite fibers and from 0.10% to 1.0% cyanoacrylate. The preferred ranges are from 0.003% to 0.008% graphite fibers and from 0.30% to 0.80% cyanoacrylate. The top coat should also include polymers that do not age rapidly or react to light.

The single coat product is a judicious choice of the above noted materials to allow for a rapid application of one coat to achieve both goals of added bonding and flexure strength. It should contain from 0.003% to 0.03% graphite fibers and from 0.5% to 4.0% cyanoacrylate. The preferred ranges are from 0.005% to 0.015% graphite fibers and from 1.5% to 2.5% cyanoacrylates.

It is possible to provide more than one coating to the nail in either of the one or two step processes, if desired, without adversely affecting the previously covered nail.

Acrylic polymers may be added to the above compositions at from 0.001% to 3.0% percent by weight to further increase the flexure and pliability of the coating film. Most desired is the addition of acrylic polymers at from 1.0% to 2.0% by weight.

EXAMPLE II

A base coat material referred to above was prepared having the following composition by weight:

| | |
|---|---|
| Base lacquer #2548-1 | 62.000% |
| Acetone | 35.475% |
| Cyanoacrylate (200+/−50 centipoise) | 2.500% |
| Graphite fiber (same as Example I) | 0.025% |
| Tinting material | trace |
| | 100% |

Base lacquer #2548-1 contains nitrocellulose and other ingredients and can be purchased from Scholls Chemical Corporation, 200 West North Ave., Northlake, Ill.

A top coat material referred to above was prepared having the following composition by weight:

| | |
|---|---|
| Base lacquer #2548-1 | 60.000% |
| Acetone | 32.495% |
| Cellovar #160 | 5.000% |
| Ethylene glycol dimethacrylate | 2.000% |
| Cyanoacrylate (200+/−50 centipoise) | .500% |
| Graphite fiber (same as Example I) | .005% |
| Tinting material | trace |
| | 100% |

Cellovar #160 contains nitrocellulose and other ingredients and can be purchased from Cellofilm Corporation, P. O. Box 223, Woodridge, N.J. 07075.

The base coat was applied first by brushing a generous coat of the material onto a nail and allowing it to dry for 15 seconds. Next, the top coat material was applied by brushing it over the base coat and allowing it to dry for 15 seconds. The coating on the nail will reach its maximum strength at between three and four hours, although the nail is usable as soon as the top coat dries. The resulting hardened coating was smooth and adherent to the nail.

EXAMPLE III

A single coat material referred to above was prepared having the following composition by weight:

| | |
|---|---|
| Base lacquer #2548-1 | 55.000% |
| Acetone | 35.990% |
| Cellovar #160 | 5.000% |
| Ethylene glycol dimethacrylate | 2.000% |
| Cyanoacrylate (200+/−50 centipoise) | 2.000% |
| Graphite fiber (same as Example I) | 0.010% |
| Tinting material | trace |
| | 100% |

The single coat material was applied by brushing it onto a nail and allowing it to dry for 15 seconds. The single coating on the nail will reach its maximum strength at between three and four hours after application, although the nail is usable as soon as the single coat dries. The resultant hardened coating was smooth and adherent to the nail.

Having illustrated and described the principles of my invention with reference to several preferred embodiments, it should be apparent to those persons skilled in the art that such invention may be modified in arrangement and detail without departing from such principles. I claim as my invention all such modifications as come within the true spirit and scope of the following claims.

We claim:

1. A composition for adhering to human nails comprising a mixture of a cyanoacrylate compound and graphite fibers.

2. The composition of claim 1 wherein the graphite fibers are translucent graphite fibers which are whitish in color.

3. The composition of claim 1 wherein the graphite fibers vary in length from approximately 1/32 inch to 5/32 inch and have a diameter ranging from 0.3 mils to 0.75 mils.

4. The composition of claim 1 wherein the graphite fibers are present in an amount from 0.003% to 0.030% by weight of the composition.

5. The composition of claim 1 wherein the graphite fibers are present in an amount from 1.0% to 4.0% by weight of the composition.

6. A composition for forming an artificial human nail comprising a mixture of:
   a cyanoacrylate compound,
   graphite fibers, and
   a hardening accelerator including a mixture of trichloro-trifluoroethane and a methylaniline compound.

7. The composition of claim 6 wherein the methylaniline compound comprises N,N-dimethyl-P-toluidine.

8. The composition of claim 7 wherein the accelerator comprises trichloro-trifluoroethane from 35% to 60% by weight and N,N-dimethyl-P-toluidine from 25% to 40% by weight.

9. The composition of claim 6 wherein the graphite fibers are translucent graphite fibers which are whitish in color and provide an artificial nail which is translucent.

10. The composition of claim 6 wherein the graphite fibers are present in lengths varying from 1/32 inch to 5/32 inch and have a diameter ranging from 0.3 mils to 0.75 mils.

11. The composition of claim 6 wherein the graphite fibers are present in an amount from 1.0% to 4.0% by weight of the composition.

12. The composition of claim 6 wherein the accelerator includes ethyl chloride to accelerate curing time and enhance heat dispersion.

13. The composition of claim 12 wherein the accelerator comprises ethyl chloride from 15% to 40% by weight of the accelerator.

14. The composition of claim 6 wherein the accelerator includes an acrylic polymer.

15. The composition according to claim 8 wherein the accelerator comprises an acrylic polymer from 1.0% to 5.0% by weight of the accelerator.

16. A method for forming an artificial human nail comprising:
   adhesively bonding a base material containing graphite fibers and cyanoacrylate to a nail;
   shaping the base material to simulate the appearance of a natural nail; and
   spraying, in the form of a mist, the base material with a hardening accelerator including a mixture of trichloro-trifluoro-ethane and a methylaniline compound to harden the base material.

17. The method according to claim 16 wherein the methylaniline compound comprises N,N-dimethyl-P-toluidine.

18. The method according to claim 17 wherein the accelerator includes ethyl chloride to accelerate curing time and enhance heat dispersion.

19. A composition for coating a human nail comprising nitrocellulose, a cyanoacrylate compound and graphite fibers.

20. The composition of claim 19 wherein the graphite fibers are translucent graphite fibers which are whitish in color to provide a translucent coat on the nail, the fibers being present in the composition in an amount from 0.003% to 0.030% by weight of the composition.

21. The composition of claim 19 comprising an acrylic polymer from 0.001% to 3.0% by weight of the composition mixture.

22. A nail composition for coating a human nail which comprises graphite fibers and a cyanoacrylate compound for increasing the adherence of the coating to the nail.

23. The nail composition according to claim 22 wherein the cyanoacrylate is present as a liquid having a viscosity varying from 100 centipoise to 600 centipoise.

* * * * *